US007955591B1

(12) United States Patent
Wehrli

(10) Patent No.: US 7,955,591 B1
(45) Date of Patent: *Jun. 7, 2011

(54) ORAL FLUID ABSORBING COMPOSITIONS AND SYSTEM FOR APPLICATION THEREOF IN A METHOD OF DENTAL ARCH TREATMENT AND TEETH RECALCIFICATION

(76) Inventor: Janet M. Wehrli, Omaha, NE (US)

(*) Notice: Subject to any disclaimer, the term of this patent is extended or adjusted under 35 U.S.C. 154(b) by 1481 days.

This patent is subject to a terminal disclaimer.

(21) Appl. No.: 11/189,254

(22) Filed: Jul. 26, 2005

Related U.S. Application Data

(63) Continuation-in-part of application No. 10/288,532, filed on Nov. 4, 2002, now Pat. No. 7,029,690, and a continuation-in-part of application No. 10/008,929, filed on Nov. 3, 2001, now Pat. No. 6,475,471, and a continuation-in-part of application No. 09/549,301, filed on Apr. 13, 2000, now Pat. No. 6,322,772.

(60) Provisional application No. 60/354,414, filed on Feb. 7, 2002, provisional application No. 60/395,822, filed on Jul. 15, 2002, provisional application No. 60/145,028, filed on Jul. 22, 1999.

(51) Int. Cl.
 *A61Q 11/00* (2006.01)
(52) U.S. Cl. .......................................... 424/49; 514/902
(58) Field of Classification Search .................... 424/49; 514/902

See application file for complete search history.

(56) References Cited

U.S. PATENT DOCUMENTS

| 3,339,547 | A | * | 9/1967 | Drabkowski | .................... 604/77 |
| 3,527,219 | A | | 9/1970 | Greenberg | .................... 128/260 |
| 3,844,286 | A | | 10/1974 | Cowen | .......................... 128/260 |
| 4,063,552 | A | | 12/1977 | Going et al. | .................. 128/861 |
| 4,173,219 | A | | 11/1979 | Lentine | ........................ 128/260 |
| 4,344,931 | A | | 8/1982 | Aguilar | ............................ 424/49 |
| 4,568,536 | A | * | 2/1986 | Kronenthal et al. | .......... 424/435 |
| 4,594,240 | A | | 6/1986 | Kawata et al. | ................ 424/447 |
| 4,812,308 | A | | 3/1989 | Winston et al. | ................. 424/49 |
| 4,813,613 | A | | 3/1989 | Salete | .............................. 241/7 |
| 4,980,391 | A | | 12/1990 | Kumar et al. | ................... 524/48 |
| 4,981,698 | A | | 1/1991 | Cherukuri et al. | ................ 426/5 |
| 5,004,595 | A | | 4/1991 | Cherukuri et al. | .............. 424/41 |
| 5,038,396 | A | | 8/1991 | Gjerlov | ......................... 424/737 |
| 5,143,728 | A | | 9/1992 | Cappel et al. | ............. 424/195.1 |
| 5,268,396 | A | | 12/1993 | Lai | ................................. 522/28 |
| 5,294,432 | A | | 3/1994 | Winston et al. | ................. 424/49 |
| 5,323,787 | A | | 6/1994 | Pratt | ............................. 128/262 |
| 5,326,685 | A | | 7/1994 | Gaglio et al. | ................. 433/215 |
| 5,445,826 | A | | 8/1995 | Kuhrts | .......................... 424/451 |
| 5,466,469 | A | | 11/1995 | Kuhrts | .......................... 424/451 |
| 5,525,652 | A | | 6/1996 | Clarke et al. | ..................... 524/37 |
| 5,562,449 | A | | 10/1996 | Jacobs et al. | .................. 433/215 |
| 5,575,654 | A | | 11/1996 | Fontenot | ...................... 433/215 |
| 5,760,102 | A | | 6/1998 | Hall et al. | ...................... 523/120 |
| 5,863,202 | A | | 1/1999 | Fontenot et al. | .............. 433/215 |
| 5,869,029 | A | | 2/1999 | Graff-Andersen et al. | ..... 424/52 |
| 5,924,863 | A | | 7/1999 | Jacobs et al. | ..................... 433/80 |
| 5,948,439 | A | | 9/1999 | Forman et al. | ................ 424/466 |
| 6,086,856 | A | | 7/2000 | Saferstein et al. | .............. 424/49 |
| 6,155,832 | A | | 12/2000 | Wiesel | .......................... 433/215 |
| 6,224,372 | B1 | | 5/2001 | Ibsen et al. | ................. 433/168.1 |
| 6,258,342 | B1 | | 7/2001 | Harcum et al. | ................. 424/49 |
| 6,287,120 | B1 | | 9/2001 | Wiesel | .......................... 433/215 |
| 6,322,772 | B1 | | 11/2001 | Wehrli | ............................ 424/49 |
| 6,350,794 | B1 | | 2/2002 | Borja | ............................. 523/120 |
| 6,475,471 | B1 | | 11/2002 | Wehrli | ............................ 424/49 |

FOREIGN PATENT DOCUMENTS

| JP | 08-245353 | * | 9/1996 |
| JP | 2000044446 | | 2/2000 |

OTHER PUBLICATIONS

Amer. Acad. Periodontology (A. A. P.) "Current Understanding of the Role of Microscopic Monitoring, Baking Soda and Hydrogen Peroxide in Treatment of Periodontal Disease" (p. 3 Footnotes 14 to 21 Home/Local Therapy With Baking Soda and Peroxide (Keyes Technique) is Known to Produce Gingival Inflammation), Apr. 1994.
"Clinical Evaluation of a Hydrogen Peroxide Mouth Rinse, Sodium Bicarbonate Dentifrice, and Mouth Moisturizer on Oral Health", Shibly et al., J. Clin Dent. vol. VIII (8), (1997).
"Local Delivery of Antimicrobial Agents in the Periodontal Pocket", Slots et al., Periodontology-2000 (1996).
"Historical View of Dentifrice Functionality Methods", Hefferren, J. Clin. Dent. IX (3) (1998).
"Evaluation of the Effects of Brushing on the Removal of Dental Plaque", Mankodi et al., J. Clin. Dent IX (3) (1998).
"Preliminary Report: Laboratory-induced Stain Removal as Assessed by Environmental Scanning Electron Microscopy", Habib et al., J. Clin. Dent. (IX(3) (1998).
"A Longitudinal Comparison of Tooth Whitening Resulting from Dentifrice", Koertge et al., J. Clin. Dent. (IX(3), (1998).
"Laboratory Assessment of Tooth Whitening by Sodium Bicarbonate Dentifrice Use", Koertge, J. Clin. Dent. IX(3), (1998).
"Dental Health Fact Sheets", Academy of General Dentistry, http://www.agd.org/consumer/facts/gumdisease.html, (1999).

(Continued)

*Primary Examiner* — Frederick Krass
*Assistant Examiner* — Chris E Simmons
(74) *Attorney, Agent, or Firm* — James D. Welch

(57) ABSTRACT

Disclosed is a method of promoting oral hygiene and teeth re-calcification involving increasing crevicular fluid flow in a subject in the presence of hydroxide containing material such that $OH^-$ ions are formed and caused to contact the teeth. The method further involves causing calcium $Ca^{++}$ ion containing material to simultaneously, or subsequently, contact the teeth.

2 Claims, 6 Drawing Sheets

OTHER PUBLICATIONS

"Enhance Bactericidal Activity of Arm and Hammer Dental Care", Drake Am J. Dent. 8(6), (1995).

"An Evidence-Based Review of Sodium Bicarbonate as a Dentifrice Agent", Barnes, Cont. Ed. in Oral Hygiene, 6(3) (1997).

Preventing Infective Endocarditis: A Review of Current Practice Protocols, J. Prac. Dent. Hyg. (1999).

"Current Understanding of the Role of Microscopic Monitoring, Baking Soda and Hydrogen Peroxide in the Treatment of Periodontal Disease", John, Committee on Research, Science and Therapy, (1994).

"Biological Therapies in Dentistry; A Bimonthly Newsletter of Dental Professionals", vol. 13, (1997).

"Delivery Systems for Agents in Supra- and Sub-gingival Plaque Control", J. Dent. Res., 68 (1989).

"The Effect of Bicarbonate/Fluoride Dentifrices on Human Plaque PH", Blake-Haskins et al., J. Clin Dent. 8 (1997).

"Toothbrushing with Hydrogen Peroxide-Sodium Bicarbonate Compared to Toothpowder and Water in Reducing Periodontal Pocket Suppuration and Darkfield Bacteria Counts", West et al., J Periodontology, (1983).

"Long Term Effects of Microbiologically Modulated Periodontal Therapy on Advanced Adult Periodonitis", Rams et al., JADA, vol. iii (1985).

"An Introduction to Subgingival Ultrasonic Scaling", Bernett, Instructional information from Dentsply International Inc.

"Incidence of Transient Bacteremia Following Dental Surgery", Katoh, J. Exp. Clin. Med. 17(3.-4) (1992).

"RI. Dental Flossing and its Relationship to Transient Bacteremia", Carroll et al., Periodontal 51(12) (1980).

"A Quantitative Measurement of Bacteremia and its Relationship to Plaque Control", Wank et al., J. Periodontal 47(12) (1976).

"Shayegania M. Bacteremia Following Dental Cleaning Patients With and Without Penicillin Prophylaxis", Baltch et al., Am Heart J. 104(6) (1982).

"Microbiological and Clinical Effects of Topical Subgingival Antimicrobial Treatment on Human Periodontal Disease" Rosling et al., J. Clin Periodontal, (1983).

"Antimicrobial Properties of Hydrogen Peroxide and Sodium Bicarbonate Individually and in Combination Against Selected Oral Gram-Negative, Faculative Bacteria", J. Dent. Res. (1986).

"The Relation of Preventive Dental Behaviors to Periodontal Health Status", Lang et al., J. Clin. Periodontal, (1994).

"Floss Away to Avoid Gum Woes", ThirdAge.com, http:/www.thirdage.com/news/archive/980813-05.html?rs, (Archive 1998).

Gum Disease: No Magic Bullet:, ThirdAge.com, http:/www.thirdage.com/news/archive/980915-03.html?rs, (Archive 1998).

"New Gel to Alter Gum Disease", ThirdAge.com, http:/www.thirdage.com/news/archive/980990-01.html?rs, (Archive 1998).

"FDA Accepts OraPhara's New Drug Application for MPTS in Adult Peridontis", OraPharma Inc. Newsletter, (Apr. 26, 2000).

"American Dental Technologies Announces Patent for Treating Periodontal Disease", American Dental Technologies Inc. News Article, (Apr. 25, 2000).

"Atrix Announces Results for Expanded Utility of ATRIDOX Periodontal Therapy", Atrix Laboratories, Ltd. News Article, (Sep. 23, 1999).

"New Analysis Reveals Human Mouth Carries More Germs Than Expected", Baxter Foundation et al. News Article, (Dec. 6, 1999).

"Top 12 Ways to Reduce your Real Age", Realage.com, http://www.realage.com/About_RA/12 ways.html., (Oct. 14, 1999).

"Periodontists Can Help Brides Achieve Gleaming Wedding Smiles", Am. Acad. of Peridontology News Article, (Sep. 16, 1997). Lordan.com, http:/www/lordan.com/pages/category.htm., The Category (Aug. 29, 1999).

"Starving Bacteria of Iron Might Prevent Periodontitis, say Researchers", J. of the Am Dental Assn., JADA, vol. 124, (Aug. 1999).

"Innovations in Toothpaste", Business Weekly, Herald-Tribune, Sarasota FL, (May 31, 1999).

* cited by examiner

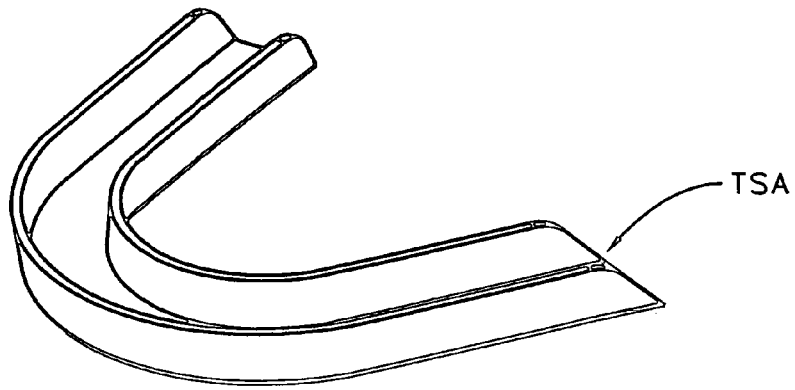
FIG. 1a
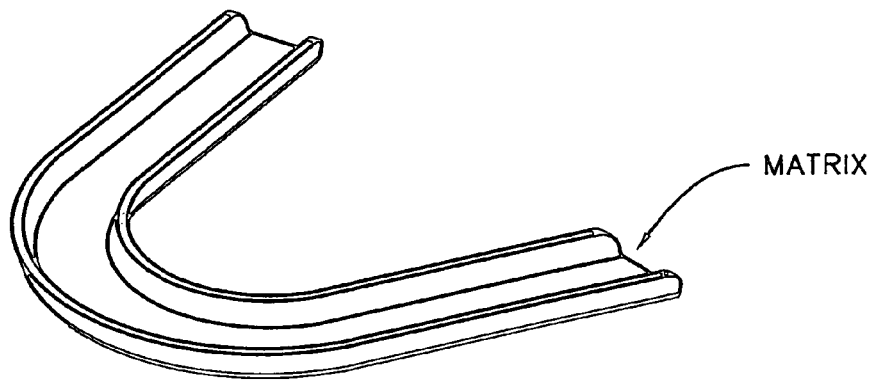
FIG. 1a'
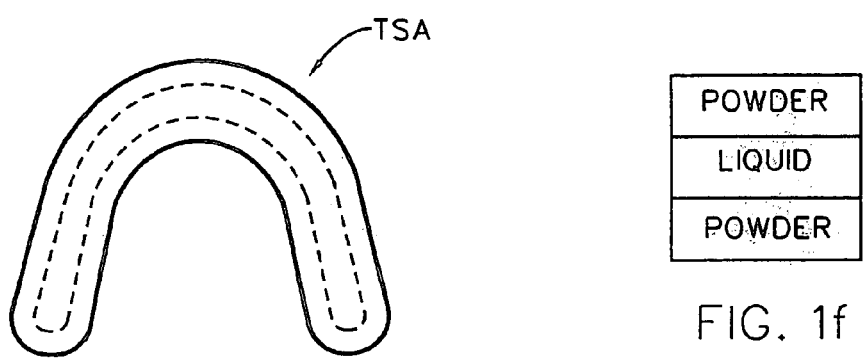
FIG. 1a''
FIG. 1f

US 7,955,591 B1

ORAL FLUID ABSORBING COMPOSITIONS AND SYSTEM FOR APPLICATION THEREOF IN A METHOD OF DENTAL ARCH TREATMENT AND TEETH RECALCIFICATION

This Application is a Continuation-In-Part of application Ser. No. 10/288,532 Filed Nov. 4, 2002 now U.S. Pat. No. 7,029,690, and therevia of Ser. No. 10/008,929 Filed Nov. 3, 2001 now U.S. Pat. No. 6,475,471; and of application Ser. No. 09/549,301 filed Apr. 13, 2000, (now U.S. Pat. No. 6,322,772); and Claims benefit of Provisional Application Ser. No. 60/354,414 Filed Feb. 7, 2002 and of 60/395,822 Filed Jul. 15, 2002; and further, via said 301 Application, this Application also Claims benefit of Provisional Patent Application Ser. No. 60/145,028 filed Jul. 22, 1999.

TECHNICAL FIELD

The disclosed invention relates to systems for use in, as well as methodology for, applying materials in mouths of subjects, and more specifically to use of tray/system/article means comprised at least partially of, and/or are caused to contain material/oral compositions which comprize hydroxide and are absorbent of oral fluids, thereby enabling prolonged application thereof to dental arches of subjects. The purpose is to induce crevicular fluid and saliva flow, cause lysing of bacteria swept thereinto; and loosen, degrade and detach dental plaque from teeth. The presence of said induced fluid serves to ionize hydroxide to OH$^-$ and present the ions to the subject's teeth. The method further includes applying calcium containing material, ionized to Ca$^{++}$ by the fluid or otherwise to the teeth.

BACKGROUND

Utility Patent Applications Ser. Nos. 10/288,532 Filed Nov. 4, 2002; 09/549,301 filed Apr. 13, 2000, (now U.S. Pat. No. 6,322,772), and 10/008,929 Filed Nov. 3, 2001, (now U.S. Pat. No. 6,475,471); and Provisional Patent Applications Serial Nos. 60/145,028 filed Jul. 22, 1999 and 60/354,414 Filed Feb. 7, 2002, are included hereinto by reference.

Typical approaches to applying dentifrice in liquid, powder, gel or paste form include tooth-brushing, flossing, rinsing and by use of pressure driven sprays. Less common, but known methods include use of self-sticking strips and impregnated finger cots.

Also known are teeth whitening agent delivery system "trays" which are of a shape to enable loose fit around teeth. In use a whitening agent is placed into said tray and the tray is then caused to be loosely positioned around a dental arch, such that the whitening agent is placed into direct contact with teeth for some period of time. Said trays, it is noted, are typically not absorbing and do not extend to access gums, particularly in the location of molars and wisdom teeth, (eg. conventionally identified as teeth numbers 1, 2, 15, 16, 17, 18, 31 and 32).

Further, in the treatment of periodontal gum disease it is known to apply antibiotics via placement of antibiotic containing carrier means under the gum in contact with teeth.

It is also known to place calcium containing materials in contact with teeth to induce recalicification thereof.

Non-Patent Materials which are known are;

"Clinical Evaluation of a Hydrogen Peroxide Mouth Rinse, Sodium Bicarbonate Dentifrice, and Mouth Moisturizer on Oral Health", Shibly et al., J. Clin. Dent. Vol. VIII(8), (1997).

"Local Delivery of Antimicrobial Agents in the Periodontal Pocket", Slots et al., Periodontology-2000 (1996).

"Historical View of Dentifrice Functionality Methods", Hefferren, J. Clin. Dent. IX(3) (1998).

"Evaluation of the Effects of Brushing on the Removal of Dental Plaque", Mankodi et al., J. Clin. Dent. IX(3) (1998).

"Preliminary Report: Laboratory-induced Stain Removal as Assessed by Environmental Scanning Electron Microscopy", Habib et al., J. Clin. Dent. (IX(3) (1998).

"A Longitudinal Comparison of Tooth Whitening Resulting from Dentifrice", Koertge et al., J. Clin. Dent. (IX (3), (1998).

"Laboratory Assessment of Tooth Whitening by Sodium Bicarbonate Dentifrice Use", Koertge, J. Clin. Dent. IX(3), (1998).

"Dental Health Fact Sheets", Academy of General Dentistry, http://www.agd.org/consumer/facts/gumdisease.html, (1999).

"Enhance Bactericidal Activity of Arm and Hammer Dental Care", Drake Am J. Dent. 8(6), (1995).

"An Evidence-Based Review of Sodium Bicarbonate as a Dentifrice Agent", Barnes, Cont. Ed. in Oral Hygiene, 6(3) (1997).

"Preventing Infective Endocarditis: A Review of Current Practice Protocols, J. Prac. Dent. Hyg. (1999).

"Current Understanding of the Role of Microscopic Monitoring, Baking Soda and Hydrogen Peroxide in the Treatment of Periodontal Disease", John, Committee on Research, Science and Therapy, (1994).

"Biological Therapies in Dentistry; A Bimonthly Newsletter of Dental Professionals", Vol 13, (1997).

"Delivery Systems for Agents in Supra- and Sub-gingival Plaque Control", J Dent. Res., 68 (1989).

"The Effect of Bicarbonate/Fluoride Dentifrices on Human Plaque PH", Blake-Haskins et al., J. Clin Dent. 8 (1997).

"Toothbrushing with Hydrogen Peroxide-Sodium Bicarbonate Compared to Toothpowder and Water in Reducing Periodontal Pocket Suppuration and Darkfield Bacteria Counts", West et al., J Periodontology, (1983).

"Long Term Effects of Microbiologically Modulated Periodontal Therapy on Advanced Adult Periodonitis", Rams et al., JADA, Vol. iii (1985).

"An Introduction to Subgingival Ultrasonic Scaling", Bernett, Instructional information from Dentsply International Inc.

"Incidence of Transient Bacteremia Following Dental Surgery", Katoh, J. Exp. Clin. Med. 17(3.-4) (1992).

"RI. Dental Flossing and its Relationship to Transient Bacteremia", Carroll et al., Periodontal 51(12) (1980).

"A Quantitative Measurement of Bacteremia and its Relationship to Plaque Control", Wank et al., J. Periodontal 47(12) (1976).

"Shayegania M. Bacteremia Following Dental Cleaning Patients With and Without Penicillin Prophylaxis", Baltch et al., Am Heart J. 104(6) (1982).

"Microbiological and Clinical Effects of Topical Subgingival Antimicrobial Treatment on Human Periodontal Disease" Rosling et al., J. Clin. Periodontal, (1983).

"Antimicrobial Properties of Hydrogen Peroxide and Sodium Bicarbonate Individually and in Combination Against Selected Oral Gram-Negative, Faculative Bacteria", J. Dent. Res. (1986).

"The Relation of Preventive Dental Behaviors to Periodontal Health Status", Lang et al., J. Clin. Periodontal, (1994).

"Floss Away to Avoid Gum Woes", ThirdAge.com, http://www.thirdage.com/news/archive/980813-05.html?rs, (Archive 1998).

"Gum Disease: No Magic Bullet:, ThirdAge.com, http://www.thirdage.com/news/archive/980915-03.html?rs, (Archive 1998).

"New Gel to Alter Gum Disease", ThirdAge.com, http://www.thirdage.com/news/archive/980990-01.html?rs, (Archive 1998).

"FDA Accepts OraPhara's New Drug Application for MPTS in Adult Periodontis", OraPharma Inc. Newsletter, (Apr. 26, 2000).

"American Dental Technologies Announces Patent for Treating Periodontal Disease", American Dental Technologies Inc. News Article, (Apr. 25, 2000).

"Atrix Announces Results for Expanded Utility of ATRIDOX Periodontal Therapy", Atrix Laboratories, Ltd. News Article, (Sep. 23, 1999).

"New Analysis Reveals Human Mouth Carries More Germs Than Expected", Baxter Foundation et al. News Article, (Dec. 6, 1999).

"Top 12 Ways to Reduce your Real Age", Realage.com, http://www.realage.com/About_RA/12 ways.html., (Oct. 14, 1999).

"Periodontists Can Help Brides Achieve Gleaming Wedding Smiles", Am. Acad. of Periodontology News Article, (Sep. 16, 1999).

Lordan.com, http:/www//lordan.com/pages/category.htm., The Category (Aug. 29, 1999).

"Starving Bacteria of Iron Might Prevent Periodontitis, say Researchers", J. of the Am Dental Assn., JADA, Vol. 124, (August 1999).

"Innovations in Toothpaste", Business Weekly, Herald-Tribune, Sarasota Fla., (May 31, 1999).

A Patent Search was conducted. The results thereof are:

U.S. Pat. No. 4,344,931 to Aguilar which describes a dry powder incorporating psyllium seed gum.

U.S. Pat. No. 4,812,308 to Winston et al., which describes sodium bicarbonate containing tooth paste.

U.S. Pat. No. 5,294,432 to Winston et al. which describes dentifrices incorporating alkali metal pyrophosphate salts and sodium bicarbonate in amounts effective to inhibit calculus formation on teeth.

U.S. Pat. No. 4,981,698 to Cherukuri et al. describes a multiple encapsulated sweetener delivery system and method of preparation in relation to psyllium.

U.S. Pat. No. 5,004,595 to Cherukuri et al. describes a psyllium delivery system.

U.S. Pat. No. 5,143,728 to Cappei et al. describes psyllium-containing compositions and methods.

U.S. Pat. No. 4,813,613 to Salete describes a process for obtention of high purity mucilage and mentions the use of sodium bicarbonate and bulk.

U.S. Pat. No. 3,339,547 to Drabkowski describes a topical arch tray for use in topical treatment of teeth and/or gums of a dental patient.

U.S. Pat. No. 3,527,219 to Greenburg describes an applicator for the treatment of teeth and/or gums with fluorides or other medications.

U.S. Pat. No. 3,844,286 to Cowen describes a resealable medicament dental carrier and method.

U.S. Pat. No. 5,323,787 to Pratt describes a custom fitted mouthpiece with medicated pad and container.

U.S. Pat. No. 5,575,654 to Fontenot illustrates an apparatus and method for whitening teeth.

U.S. Pat. No. 5,863,202 to Fontenot describes a system and method for treatment of dentition.

U.S. Pat. No. 5,038,396 to Glerlov is disclosed as it mentions use of bicarbonate.

U.S. Pat. No. 5,466,460 to Kuhrts is disclosed as it describes use of psyllium fiber and sodium bicarbonate.

U.S. Pat. No. 5,869,029 to Graff-Anderson et al. is disclosed as it describes use of psyllium fiber in tooth paste.

U.S. Pat. No. 5,948,439 to Forman et al. is disclosed as it mentions use of sodium bicarbonate.

U.S. Pat. No. 6,086,865 to Saferstein et al. is disclosed as it describes use of sodium bicarbonate in oral compositions.

U.S. Pat. No. 5,445,826 to Kuhrts is disclosed as it describes use of sodium bicarbonate and psyllium fiber in drug delivery systems.

U.S. Pat. No. 6,258,342 to Harcim et al. is disclosed as it describes use of psyllium in the making of toothpaste.

Patents which describe treatment of gum disease are:

U.S. Pat. No. 6,280,708 to Tyles et al., which describes a peroxide as the active agent peroxide, with mention of bicarbonate and humectants.

U.S. Pat. No. 5,846,570 to Barrow et al. describes a peroxide based dentifrice in combination with humectants.

U.S. Pat. No. 5,695,745 to Barton et al. describes treatment of Gum Disease with anti-microbials.

U.S. Pat. No. 5,632,972 to Williams et al. describes a composition of glycerol with bicarbonate.

U.S. Pat. Nos. 5,455,024 and 5,385,727 to Winston et al. describes a composition of bicrabonate, antimicrobial and a humectant.

U.S. Pat. No. 5,380,530 to Hill describes a chewing gum which includes anti-microbials.

U.S. Pat. No. 5,094,843 to Mazzonobile et al. describes an antimicrobial toothpaste.

U.S. Pat. No. 4,983,379 to Schaeffer describes a dental preparation and method for delivery thereof.

What was specifically not found was methodology utilizing tray/system/article means for application in a non-invasive method of applying absorbent materials and/or oral compositions, (eg. as a mixture of bicarbonate of soda or potassium and psyllium fiber for absorbing oral fluids), said tray/system/article means being shaped to enable containing material/oral composition for absorbing oral fluids, and said tray/system/article means being of an appropriate shape and size to fit to at least one dental arch, or portion thereof, of a subject, and itself typically being at least partially made of absorbing material. The method use of said tray/system/article means enables placing material/oral composition which absorbs oral fluids into contact with at least one dental arch, or portion thereof, of a subject to the end that crevicular fluid flow is enhanced, with accompanying sweeping and lysing of bacteria present along therewith. Further, nothing obviated the simultaneous or subsequent application of calcium to the teeth of the subject.

In view of the prior art, there remains need for tray/system/article means, including identification of oral compositions for application therein, in combinations with methodology of applying absorbing materials and/or oral compositions for absorbing oral fluids, to dental arch gum tissue of subjects, particularly where a subject presents with periodontal gum disease. It would also be of benefit if a technique which facilitates treatment of gums and teeth, could also could be adapted to sequentially or simultaneously encourage recalicification of teeth.

DISCLOSURE OF THE INVENTION

The invention disclosed in this Specification comprises a method of promoting oral hygiene involving inducing increased saliva, and crevicular fluid flow at the interface between teeth and dental arch gum tissue of a subject, said dental arch being comprised of teeth and gum material. Said method comprises the steps of:

a) providing means for absorbing oral fluids, said means for absorbing oral fluids being of an appropriate shape and size to fit to at least one dental arch, or portion thereof, of said subject, such that said means for absorbing oral fluids can be used to place absorbent material/oral composition into contact with said at least one dental arch, or portion thereof, of said subject at and about the interface between the teeth and gum tissue;

b) placing said means for absorbing oral fluids into a subject's mouth so that oral fluid absorbent material/oral composition is placed into contact with at least one dental arch, or portion thereof, at and about the interface between the teeth and dental arch gum tissue of said at least one dental arch, or portion thereof.

It is noted that preferred, but non-limiting absorbing material, comprises sodium and/or potassium bicarbonate, in combination with psyllium fiber.

Said method further comprises the step of:

c) providing means for containing calcium containing material, said means for containing calcium containing material being of an appropriate shape and size to fit to teeth in at least one dental arch, or portion thereof, of said subject, such that said means for containing calcium containing material can be used to place calcium containing material into contact with the teeth of said at least one dental arch, or portion thereof, of said subject;

d) placing said means for containing calcium containing material into said subject's mouth so that said calcium containing material is placed into contact with the teeth of at least one dental arch, or portion thereof.

It is noted that step d benefits from the inducing of saliva flow to cause the calcium to ionize.

A modified method of promoting oral hygeine of a subject comprises the steps of:

a. identifying a subject in which at least one dental arch selected from the group consisting of:
  upper; and
  lower;
thereof is to be treated, said dental arch being comprised of gums and teeth;

b. providing a means for containing hydroxide containing sodium and/or potassium-bicarbonate, and/or psullium husk fiber for absorbing oral fluids, and causing said material which absorbs oral fluids, in addition to a calcium containing material, to be contained therewithin, said means for containing material for absorbing oral fluids being of an appropriate shape and size to loosely fit to at least one dental arch of said subject, such that said material which absorbs oral fluid can be placed into contact with said at least one dental arch whereat said gums and teeth thereof meet by positioning said means for containing material for absorbing oral fluids into loose contact with at least one dental arch of said subject;

c. positioning said means for containing material for absorbing oral fluids, in loose contact with at least one dental arch of said subject such that said material for absorbing oral fluids in placed into direct contact with at least one dental arch of said subject;

such that increased saliva and crevicular fluid flow is induced, leading to solvation of said hydroxide containing material to the end that $OH^-$ ions, in addition to calcium become present at the location of the teeth.

It is noted that the OH ions serve to neutralize $H^+$ ions caused by the presence of bacteria, and to ionize Ca to $Ca^{++}$, which is actually the form of Ca that recalicifis teeth.

To aid with understanding, material substantially as presented in Parent Application, Ser. No. 10/288,532 is presented directly. Said 532 Application disclosed that the invention involves both system, (herein variously referred to as system, system means, article, article means, tray or tray means), and oral compositions and methodology or applying absorbent material and/or oral compositions to gum tissue in the mouths of subjects. The system is preferably, but not necessarily, of single piece construction, and in use is caused to be placed into contact with at least one dental arch, or portion thereof, of a subject in a manner conducive to enhancing crevicular fluid flow. A purpose of providing absorbent material/oral composition is to provide application of therapeutic/cleansing agents for an effective period of time. A purpose of inducing saliva and crevicular fluid flow, it should be appreciated, is to sweep bacteria from between teeth and gums in a subject and to ionize the bicarbonate into $OH^-$ ions, (along with $NA^+$ and $CO_2$ gas). The system is itself preferably, but not necessarily, made fully of oral fluid absorbing material which sevres to avoid overloading of the mouth with free liquid, and typical usage provides that said article means be caused to contain an oral composition for absorbing oral fluids. Functionally equivalent articles of multiple piece construction are to be considered within the scope of the Claimed Invention. The disclosed invention further comprises identification of oral compositions which are conducive to enhancing or inducing saliva and crevicular fluid flow when placed into contact with a subject's gums at the point whereat teeth emerge therefrom. The method of the disclosed invention comprises utilizing said system to apply oral composition, induce fluid flow and absorb oral fluids to at least one dental arch, or portion thereof, of a subject. Further, the word "subject" in this specification can be interpreted to mean a patient, but should be considered broadly to include any person whether afflicted or not by one or more periodontal/gingival related abnormality, (including serious bacteria caused disease and even plaque), and even animals where appropriate system article means is available.

Again, the presence of $OH^-$ ions neutralize $H^+$ ions and the presence of $Ca^{++}$ serve to recalcify teeth.

The disclosed invention system can be further described as an article means, (for inducing crevicular fluid flow), which as viewed in frontal elevation vertical cross-section over at least a majority of its extent, comprises a "U" shape of a size appropriate for being fit over at least one dental arch, or portion thereof, of a subject. The disclosed system article means can be two sided with both "U" and inverted "U" shapes present as so viewed, for use in simultaneous treatment of both upper and lower dental arches. The "U" shape(s) are of a size such that when said article means per se., or said article means with absorbent oral composition placed thereinto is placed into the mouth of a subject, absorbent system article material and/or oral composition is caused to contact, and remain in contact with the subjects dental arch gum tissue at the location where said gum tissue meets the teeth, said article being characterized by at least one selection from the group consisting of:

it is at least partially made of a material which absorbs oral fluids;

it is of a size and shape so as to locate fluid flow stimulating absorbent oral composition where it is conducive to inducing saliva and crevicular fluid flow; and it is of a size to simultaneously enable causing oral composition which absorbs oral fluids to contact gum tissue in the vicinity of the location of molar and wisdom teeth, as well as gums in the vicinity of the frontal teeth of at least one dental arch.

While a subject's oral fluid can serve as a wetting agent, the preferred embodiment involves adding a wetting agent to absorbent material(s) which absorbs oral fluids, (eg oral composition), which can be optimally selected to comprise at least one selection from the group:

sodium bicarbonate;
potassium bicarbonate;
sodium containing compound(s) other than sodium bicarbonate;
potassium containing compound(s) other than potassium bicarbonate;
a mixture of potassium bicarbonate and psyllium husk fiber;
a mixture of sodium bicarbonate and psyllium husk fiber;
a mixture comprising for each 2 & ⅔ cups sodium or potassium bicarbonate, ½ cup or less psyllium husk fiber;
calcium containing material;
ascorbic acid;
psyllium husk fiber;
starch;
cellulose;
lignin;
hemicelluloses (pentosans);
insoluable pectins;
enzyme resistant starches;
soluble gums;
soluble pectins;
soluble polysaccarides;
rice bran;
soy fiber;
beet fiber;
pea fiber;
apple pectin;
starch;
cellulose;
xanthan gums;
gum arabic;
wheat glutin;
rye glutin;
barley glutin;
oat glutin.

The absorbent material which absorbs oral fluids can be, but is not necessarily, selected to comprise a wetting, (ie. moistening), agent such as a selection from the group:

sorbitol;
xylitol;
potable water;
hydrogen peroxide;
alcohol
glycerine.

It is preferred, however, that a subject's oral fluid also performs the function of a moistening agent.

Non-limiting mixtures of materials which provide utility are:

mixture comprising sodium bicarbonate and a material which demonstrates absorbing and/or expanding properties;
mixture comprising potassium bicarbonate and a material which demonstrates absorbing and/or expanding properties;
mixture comprising potassium bicarbonate and psyllium fiber;
mixture comprising calcium and a material which demonstrates absorbing and/or expanding properties.
mixture comprising sodium bicarbonate and potassium bicarbonate;
mixture comprising sodium bicarbonate and calcium;
mixture comprising potassium bicarbonate and calcium;
mixture comprising sodium bicarbonate and potassium bicarbonate and calcium.
sodium containing compound(s) other than sodium bicarbonate;
potassium containing compound(s) other than potassium bicarbonate.

Other combinations and mixtures which can be formed from those materials identified and listed above are within the scope of the invention.

It is noted that, when used, the preferred moistening agent is potable water, but sortitol and/or xylitol and/or hydrogen peroxide and/or alcohol and/or glycerine and/or other wetting agent(s) can be utilized within the scope of the disclosed invention. However, it is to be understood that wetting agents are not absolutely necessary. It is further noted that the resulting material can be termed a "composition of matter", which is placed into an article means during use.

It is to be appreciated that psyllium husk fiber is identified as a particularly relevant material which demonstrates absorbing and/or expanding properties, when placed into contact with oral fluids, but that any functionally equivalent material(s) can be substituted therefore. Further, said oral composition for absorbing oral fluid can be selected to comprise at least one antimicrobial agent as well. When present, the antimicrobial agent(s) may be selected based upon results of analysis of the microbes present in a subject's gum tissue as determined by performing an analysis thereof. Examples of suitable candidates are tetracycline, doxycycline, chlorhexidine, penicilins, cephalosporins, macrolides, amoxicillin, and other miscellaneous antimicrobials, antifungal agents and antiviral agents.

A nominal time for application of absorbent materials and/or oral composition which absorbs oral fluids is dependent upon the individual oral environment. Time of application will then vary from case to case, and in that light, where application is, for instance, several minutes, it is noted that flavoring might be added to make the application more pleasant.

The article means can be generic or custom formed in conjunction with dental procedures such as used to mediate crown production. And again, it can be single or double sided to treat one dental arch, or both upper and lower dental arches simultaneously. Where the means for containing oral composition for absorbing oral fluids is single sided, practice of the method can involve tending upper and lower dental arches sequentially, in either order.

It is specifically to be understood that a disclosed invention article means can be made of a material which itself absorbs oral fluids, optionally in functional combination with bacterial lysing and/or static or cidal materials, thereby making placement of additional material(s) which absorb oral fluids thereinto optional. The preferred oral composition is expansive when oral fluid is absorbed thereinto, such that progressively better contact to subject dental arch gum tissue is achieved during an application period. In this case, the material/oral composition for absorbing oral fluid is present as an integral part of the system article means. Even where this is the case, however, additional material(s) for absorbing oral fluids can be caused to be contained in said article means.

It is emphasized that the present invention can involve treating both upper and/or lower dental arches of a subject simultaneously or in sequential order, with either upper or lower then being treated first.

Further, the disclosed invention includes providing a plurality of article means, (ie. trays), of different sizes and forms, such that one thereof is most appropriate for use by a specific subject, (eg. adult male, adult female or child etc.), or for a specific dental need.

The disclosed invention system can also be described as comprising an article for application in a method of treating upper and/or lower dental arches of an identified subject, particularly, (but not limited to), where said subject has periodontal gum disease. The preferred disclosed invention method comprises providing an article for containing oral composition for absorbing oral fluids and causing oral composition which absorbs oral fluids to be contained therewithin. Said article for containing material for absorbing oral fluids is preferably made fully of an absorbent material and is selected to be of an appropriate shape and size to fit to at least one dental arch of said subject, however, said article for containing material for absorbing oral fluids can be only partially made of an absorbent material, or, importantly, contain no absorbent material where absorbent material is caused to be present therein as by, for instance, being lined with absorbent material. In use, practice of the disclosed invention provides that material which absorbs oral fluid is placed into contact with said at least one dental arch, or portion thereof, of a subject by positioning said article for containing material for absorbing oral fluids into contact with at least one dental arch, or portion thereof, of said subject, such that said material for absorbing oral fluids is placed into direct contact with at least one dental arch, or portion thereof, of said subject.

As the preferred method of application involves various times of application, one embodiment of the presently disclosed invention article means further comprises a hole in the "front" thereof, (ie. front is near where the front teeth, nos. 8 & 9 & 23 & 24, are contacted), through which a subject can breath. Further, a straw-like means can be placed into the hole and simultaneously additionally serve as an aid to insertion and removal of the article means from a subject's mouth via suction. Another modification provides that depressions be placed where the crowns of teeth contact the article means when it is properly positioned in a subject's mouth. Another variation provides for application of vacuum fluid removal. In addition, oral fluids can be removed through the straw-like tube, or similar arrangement.

It is also disclosed that the Inventor/Applicant has observed that noticeable whitening of teeth can be effected by prolonged, (eg. 30 minutes or more), or by repeated application of oral composition thereto, (eg. such as the mixture of sodium bicarbonate and psyllium fiber when held in contact with the teeth by a disclosed invention tray).

It is to be understood that said article means can be selected from a plurality of similarly shaped, but differently size-scaled articles. Various modifications of a basic shape are also within the scope of the disclosed invention. The purpose of the article, however, guides its design and selection, said purpose being to place oral fluid flow stimulating absorbent oral composition(s) in contact with, and about, the interface between teeth and dental arch gum tissue in a manner which is conducive to inducing saliva and crevicular fluid flow out of the interface between the teeth and dental arch gum tissue from below the gum tissue line, into the absorbent material.

It is also to be understood that absorbent materials typically expand when they absorb fluid, and in that light the term "absorbent" is to be read as including materials which expand when exposed to fluid. Some materials, (eg. psyllium, cotton, oat fiber among others), expand more than others and can be included primarily for that aspect. Such materials, for the purpose of this Specification are to be considered as within the definition of the term "absorbent". Other terms which help to define the essence of the term "absorbent", as it is used herein, are "osmotic-pressure-inducing", "lysing", "dehydrating", "enmeshing" and optionally "anti-microbial", "bacteriostatic" and "bacteriocidal".

It is also noted that introducing antimicrobial agents to the gingival tissue supra and subgingivally via a tray/article/system means, enables maintaining said antimicrobial agents in contact with gingival tissue for an optimum time at an effective concentration, (ie. topical local application), including time released paradigms.

It is also to be understood that the terminology "absorbing" and the like as used to describe an article means includes within its scope article means which are only partially made of absorbing material(s) or contain none at all. For instance, an article means shaped to fit to at least one dental arch, or portion thereof, of a subject can be made of a non-absorbing material and be lined with absorbing material, such as an oral composition or material. While not preferred, such an embodiment is disclosed as specifically within the scope of the disclosed invention and within the definition of "absorbent" material.

It is also to be understood that an induced flow of crevicular fluid can sweep disease causing bacteria etc. along into absorbent material. Where dental arch gum tissue is diseased, crevicular fluid flow can be expected to provide a beneficial influence.

It is to be understood that the terminology absorbent material/oral composition specifically includes tray/article/system means materials which are "hygroscopic". In particular, where a tray/article/system means is comprised of absorbent material and absorbent oral composition is placed thereinto, said absorbent materials can serve to remove oral fluids caused by crevicular fluid flow, thereby maintaining components, such as antimicrobials, therewithin at an effective concentration for an effective period of time. The Claims which recite the presence of both absorbent tray/article/system means and absorbent oral composition therewithin should be read with said described concept of hygroscopic-action in mind.

It is also to be appreciated that article means for containing material for absorbing oral fluids with oral composition which absorbs oral fluids therewithin can then be characterized by being at least one selection from the group consisting of:

a single sided tray/system/article means for contacting one dental arch, or portion thereof;

a double sided tray/system/article means for contacting two dental arches, or portions thereof;

a single or double sided tray/system/article means for contacting one dental arch, or portions thereof, in which is present an absorbent insertable matrix;

a single or double sided tray/system/article means for contacting one dental arch, or portions thereof, in which is present an absorbent insertable matrix comprised of a sealed sequence of moistening and solids materials which can be mixed by, for instance, a subject biting down thereupon;

a single or double sided tray/system/article means for contacting one dental arch, or portions thereof, which comprises a handle;

a single or double sided tray/system/article means for contacting one dental arch, or portions thereof, which comprises a breathing tube;

a single or double sided tray/system/article means for contacting one dental arch, or portions thereof, which comprises multiplicity of pockets therein for use in securing oral composition;

a single or double sided tray/system/article means for contacting one dental arch, or portions thereof, which comprises multiplicity of pockets therein which are shaped and positioned to accept a subject's teeth;

a single or double sided tray/system/article means for contacting one dental arch, or portions thereof, which comprises a multiplicity of projections extending therefrom;

a single or double sided tray/system/article means for contacting one dental arch, or portions thereof, which comprises a multiplicity of bristles projecting therefrom.

a single or double sided tray/system/article means for contacting one dental arch, or portions thereof, which is comprised of a material into which is impregnated oral composition;

a single or double sided tray/system/article means for contacting one dental arch, or portions thereof, which comprises a liner therewithin similar to those applied in teeth whitening;

a single or double sided tray/system/article means for contacting one dental arch, or portions thereof, which comprises liner piece of material which is folded to form a "V" shape;

a single or double sided tray/system/article means for contacting one dental arch, or portions thereof, which comprises suction means for removing oral fluids incorporated thereinto;

a single or double sided tray/system/article means for contacting one dental arch, or portions thereof, which comprises a linear "H" shaped article which is flexible and can be shaped to fit a subject's upper and/or lower dental arch;

a partial single or double sided tray/system/article means for contacting one dental arch, or portions thereof for treating one or more specific portions of a subject's upper and/or lower dental arches.

It is also noted that the disclosed invention can be applied to introduce both systemically active substances which are absorbed through gingival material, and locally active sunstances that combine with tooth enamel.

The present invention also teaches application of a calcium containing material primarily to the teeth of a subject after practice of the methodology which induces increased crevicular fluid flow. The rationale of the additional step is that as a byproduct of inducing increased crevicular fluid flow in the presence of hydroxide containing materials, $OH^-$ ions are caused to contact the subject's teeth. It has been found that this contact of OH ions with plaque breaks-up the plaque which has been deposited by bacteria by interfering with polysacaride bonds therebetween, thereby providing teeth surfaces which are not blocked by such deposits. The presence of $OH^-$ ions which facilitate this are increased naturally by saliva and crevicular fluid flow. The $H^+$ ions present in plaque lower the pH of a tooth surface to cause $Ca^+$ to go into solution, thus causing tooth de-calcification. $OH^-$ ions thus have a doubly good effect as they both neutralize $H^+$ ions and encourage re-calcification of teeth. While the calcium containing material can be simply mixed with the hydroxide containing material, a preferred approach is to practice the methodology as described above, followed by a seperate step which causes calcium cointaining material to be placed into contact with the subject's teeth using a similar delivery system, (eg. a tray/system/article means which faciliatates placing calcium ion $Ca^{++}$ containing material into contact with teeth which is relatively free of plaque).

For insight it is noted that a chemical equation which is involved in tooth dymanics is: $(Ca^{++})_{10} = (PO_4^{-3})_6 + (OH^-)_2$.

This equation applies to describe removal of $Ca^{++}$ from teeth during tooth decay, and to describe, in the opposite direction, recalcification of teeth.

Absorbent oral composition which absorbs oral fluid and/or calcium containing mateials which is caused to be contained within said tray/system/article can be provided in any form, such as powder(s), moistened powder(s), paste and gel, etc. Use of any form of said absorbent oral composition and/or calcium containing material is within the scope of the Claims.

It is also noted that the absorbent oral composition material can be applied by brushing and/or swabing. This can be of benefit where the adhesive properties of psyllium fiber are used to secure other materials to the gums. That is, psyllium fiber can form a quasi form-fitted tray.

Finally, it is noted that the methodology disclosed in the preceeding can be supplemented by a step involving packing material into the pockets formed between teeth and surrounding gum tissue to further enhance the identified effects. For instance, $OH^-$ and $CA^{++}$ ions can be positioned in contact with teeth below the gums thereby. Incorporating psyllium fiber into the material packed into the pockets serves to secure other materials present in place, where otherwise they would be quickly washed out.

The disclosed invention will be more clearly understood by reference to the Detailed Description Section of this Application in conjunction with the Drawings.

SUMMARY OF THE INVENTION

It is therefore a purpose and/or objective of the present invention to teach tray/system/article means, with numerous non-limiting specific examples thereof being provided elsewhere in this Specification, for use in treating upper and/or lower dental arches, or parts thereof, of a subject, particularly where said subject has periodontal gum disease.

It is another purpose and/or objective of the present invention to teach methodology of treating upper and/or lower dental arches of a subject, with specific non-limiting examples thereof being provided elsewhere in the Specification, via inducing flow of crevicular fluid, particularly where said subject has periodontal gum disease, or periodontally/gingivally related abnormality.

It is another purpose and/or objective yet, of the present invention, to teach a method of treating upper and/or lower dental arches, or parts thereof, of a subject, particularly but not limited to where said subject has periodontal gum disease, which method is mediated by use of an absorbing article means or oral composition means, such that in use placing said absorbing article or oral composition means into contact with at least one dental arch, or portion thereof, of said subject, causes said absorbing article means to be placed into direct contact with at least one dental arch, or portion thereof, of said subject.

It is another purpose and/or objective yet, of the present invention, to teach a method of treating upper and/or lower dental arches of a subject to eliminate bacteria and toxins from between gums and teeth in a subject.

It is yet another purpose and/or objective of the present invention to teach compositions of matter which are applicable in removing bacteria from a subject's mouth.

It is another purpose and/or objective of the present invention to teach a method for improving personal oral hygiene, including promoting the whitening and recalcification of teeth.

It is another purpose and/or objective of the present invention to teach the introduction of antimicrobial agents to the gingival tissue both supra and subgingivally, such that said agents are held in place by said tray/system/article means and remain at an effective concentration over a prescribed contact time or are time released, via, for example hygroscopic action of material from which said tray/system/article means is comprised.

It is another purpose and/or objective of the present invention to teach the introduction of systemically active agents via a tray/system/article means.

It is another purpose and/or objective of the present invention to teach application of calcium containing material primarily to the teeth of a subject simultaneous with, or after practice of the methodology which induces increased crevicular fluid flow, utilizing similar tray/system/article means for delivery.

Other purposes and/or objectives of the present invention will become apparent by a reading of the Specification and the Claims.

BRIEF DESCRIPTION OF THE DRAWINGS

FIG. 1a demonstrates, in perspective, a non-limiting embodiment of a disclosed invention tray/system/article means.

FIG. 1a' demonstrates, in perspective, an insertable matrix which can be applied to the system of FIG. 1a.

FIG. 1a" shows a top view of the insertable matrix of FIG. 1a' inserted into the system of FIG. 1a FIGS. 1c-1e show cross-sectionals taken on FIG. 1b.

FIG. 1f demonstrates that an insertable matrix can be comprised of a sealed sequence of moistening and solids materials which can be mixed by, for instance, a subject biting down thereupon.

DETAILED DESCRIPTION

Turning now to the Drawings, FIG. 1a demonstrates, in perspective, a non-limiting single sided embodiment of the disclosed invention tray/system/article means (TSA) for use in practicing the disclosed invention method. As oriented, (ie. opening upward), it would be applicable to use on a subject's upper dental arch, and if turned over, (ie. so that it opens downward), would be applicable to use on a subject's lower dental arch. Typically said tray/system/article means (TSA) is made of a material which absorbs induced crevicular fluid during use, however, the disclosed invention includes the case where the tray/system/article means (TSA) is made of either an absorbent or non-absorbent material, but an absorbent matrix (M) as shown in FIG. 1a' is inserted thereinto during use. FIG. 1a" shows a top view of the insertable matrix of FIG. 1a' inserted into the system of FIG. 1a. The insertable matrix (M) is best understood as comprising a material in which is present, (eg. by impregnation into preformed material or inclusion during material formation for instance), crevicular fluid flow inducing and/or enhancing materials.

FIG. 1f demonstrates that an insertable matrix, as demonstrated in FIG. 1a', can be comprised of a sealed sequence of moistening agents and solids materials, (eg. H2O and a powder), which can be mixed by, for instance, a subject biting down thereupon when it is placed into an upper of lower portion of a tray/system/article means (TSA).

Figure 2:
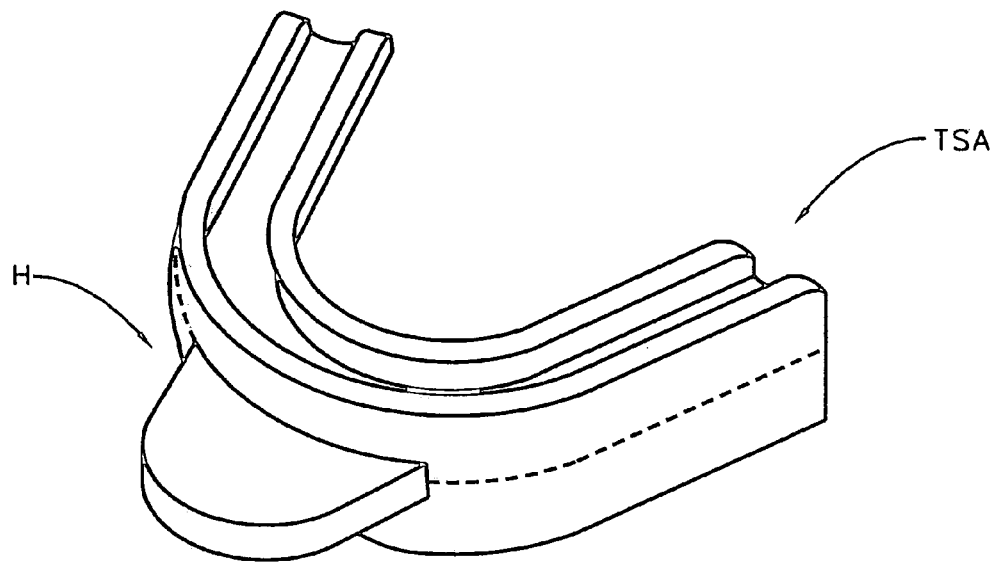
FIG. 2 demonstrates a non-limiting embodiment of a two sided tray/system/article means.

FIG. 2 demonstrates a non-limiting two sided embodiment of the disclosed invention tray/system/article means (TSA) which is shown with an optional handle (H) means, said two sided embodiment being useful for use in treating both upper and lower dental arches of a subject. (It is specifically stated that the Handle (H) does not have to be present in FIG. 2a, but is shown as present as demonstrative of an option which can be applied to any demonstrative embodiment).

Figure 3:
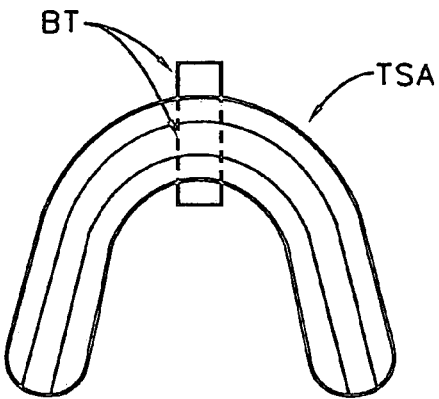
FIG. 3 demonstrates a non-limiting embodiment of the disclosed invention tray/system/article means which includes a breathing tube.

FIG. 3 demonstrates a non-limiting embodiment of the disclosed invention system which includes a breathing tube (BT). This is useful where a subject finds it difficult to breath while the tray/system/article means (TSA) is inserted into his or her mouth, particularly when crevicular fluid flow is induced.

Figure 4:
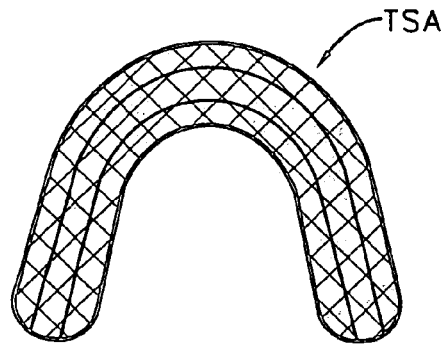
FIG. 4 demonstrates a top view of a tray/system/article means for use practicing the disclosed invention method characterized with a multiplicity of pockets therein for use in securing oral composition.

FIG. 4 demonstrates a top view of a tray/system/article means (TSA) for use practicing the disclosed invention method characterized with a multiplicity of pockets (PK) therein for use in securing oral composition.

Figure 5:
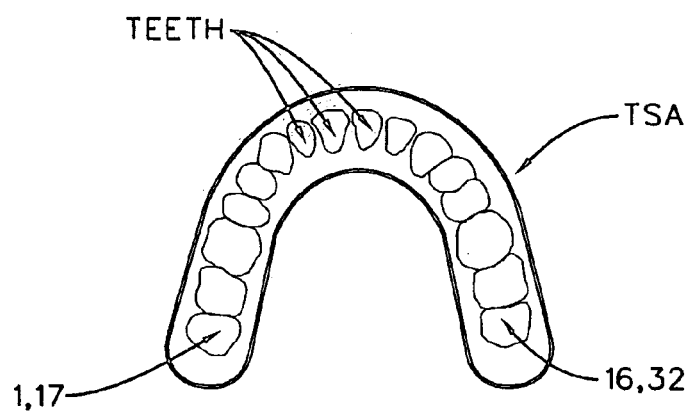
FIG. 5 demonstrates a top view of a tray/system/article means for use practicing the disclosed invention method characterized with a multiplicity of pockets therein which are shaped and positioned to accept a subject's teeth.

FIG. 5 demonstrates a top view of a tray/system/article means (TSA) for use practicing the disclosed invention method characterized with a multiplicity of pockets (TE) therein which are shaped and positioned to accept a subject's teeth. The allows better fitting of the tray/system/article means (TSA).

Figure 6:
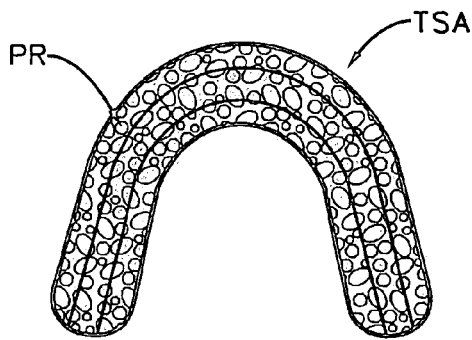
FIG. 6 demonstrates a top view of a tray/system/article means for use practicing the disclosed invention method characterized with a multiplicity of projections extending therefrom.

FIG. 6 demonstrates a top view of a tray/system/article means (TSA) for use practicing the disclosed invention method characterized with a multiplicity of projections (PR), (eg. similar to rubber tooth picks on the ends of some toothbrushes), extending therefrom.

Figure 7:
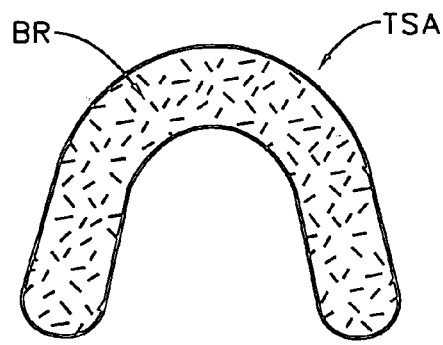
FIG. 7 demonstrates a top view of a tray/system/article means for use practicing the disclosed invention method characterized with a multiplicity of bristles projecting therefrom.

FIG. 7 demonstrates a top view of a tray/system/article means (TSA) for use practicing the disclosed invention method characterized with a multiplicity of bristles (BR), like toothbrush bristles, projecting therefrom.

Figure 8:
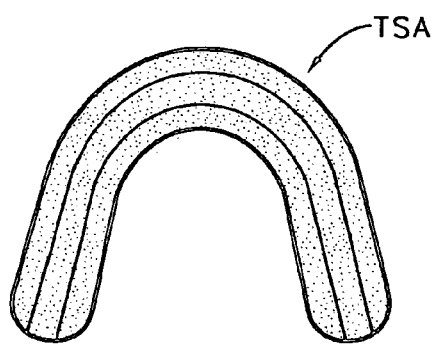
FIG. 8 demonstrates a top view of a tray/system/article means for use practicing the disclosed invention method characterized by being comprised of a material into which is impregnated oral composition.

FIG. 8 demonstrates a top view of a tray/system/article means (TSA) for use practicing the disclosed invention method characterized by being comprised of a material into which is impregnated (IMP) oral composition. That is, FIG. 8 is included to specifically focus disclosure on fashioning a tray/system/article means (TSA) which is per se. made of material which comprises oral composition.

Figure 9:
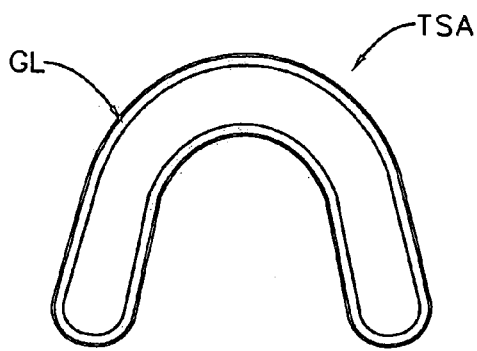
FIG. 9 demonstrates a top view of a tray/system/article means for use practicing the disclosed invention method characterized by having a liner therewithin similar to those applied in teeth whitening.

FIG. 9 demonstrates a top view of a tray/system/article means (TSA) for use practicing the disclosed invention method characterized by having a liner which comprises a glue or adhesive (GL) like material therewithin, similar to that found in teeth whitening strips.

Figure 10:
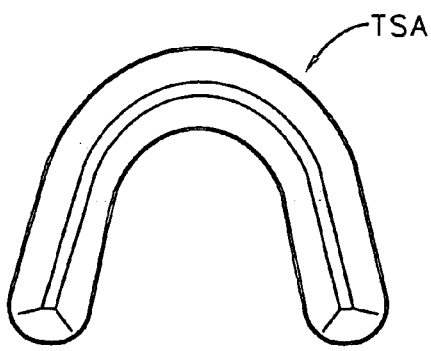
FIG. 10 demonstrates a top view of a tray/system/article means for use practicing the disclosed invention method characterized by being a liner piece of material which is folded to form a "V" shape.

FIG. 10 demonstrates a top view of a tray/system/article means (TSA) for use practicing the disclosed invention method characterized by being a liner piece of material which is folded to form a "V" shape, and then shaped into the shape appropriate to fit to a subject's dental arch.

Figure 11:
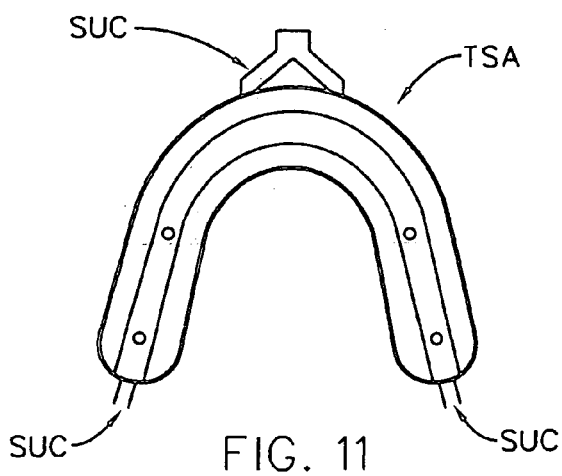
FIG. 11 demonstrates a top view of a tray/system/article means for use practicing the disclosed invention method characterized by having oral fluid removing suction means therewithin.

FIG. 11 demonstrates a top view of a tray/system/article means (TSA) for use practicing the disclosed invention method characterized by having oral fluid removing suction means (SUC) therewithin.

Figure 12A:
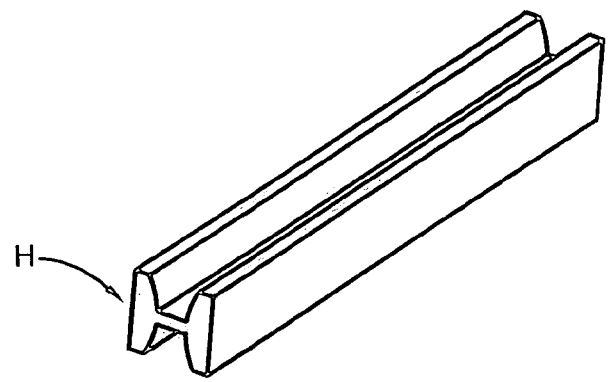
FIGS. 12a, 12b and 12c demonstrate formation of a tray/system/article means for use practicing the disclosed invention method which is formed from a linear "H" shaped article.
Figure 12B:
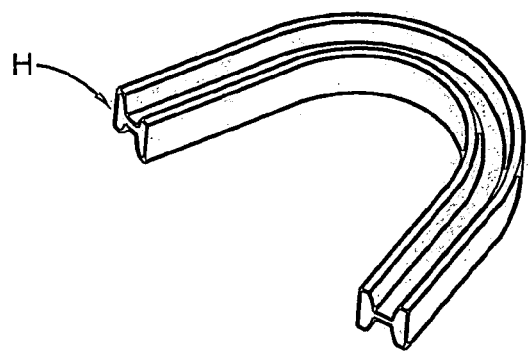
Figure 12C:
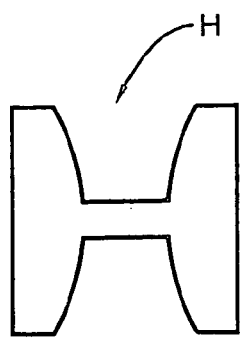

FIG. 12b demonstrates a tray/system/article means (TSA) for use practicing the disclosed invention method which is formed from a linear "H" shaped article as shown in FIG. 12a. FIG. 12c shows an end elevational view. The material is typically selected to be absorbent foam.

Figure 13:
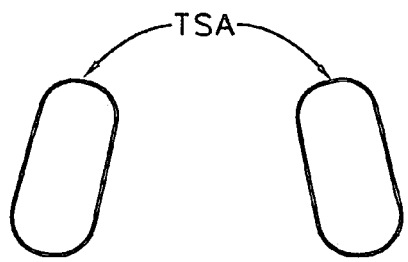
FIGS. 13 and 14 show partial tray/system/article means for use practicing the disclosed invention method.
Figure 14:
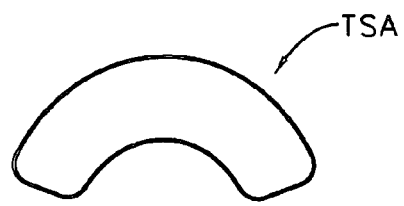

FIGS. 13 and 14 show partial tray/system/article (TSA) means for use practicing the disclosed invention method. FIG. 13 shows partial tray/system/article (TSA) means for accessing at least one side of a subject's dental arch, and FIG. 14 shows a tray/system/article (TSA) means for accessing at least one subject frontal dental arch.

Figure 15:
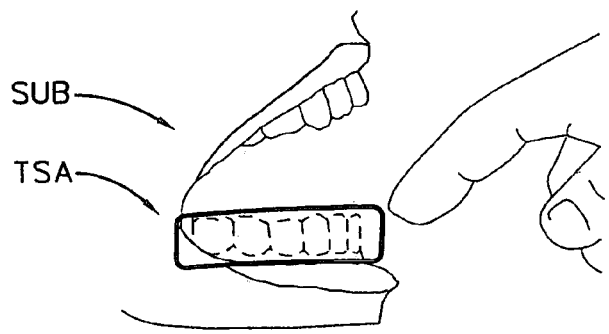
FIGS. 15, 16 and 17 show, in side elevation, tray/system/article means for use practicing the disclosed invention method placed into a subject's mouth so as to contact bottom, top and both bottom and top gums.
Figure 16:
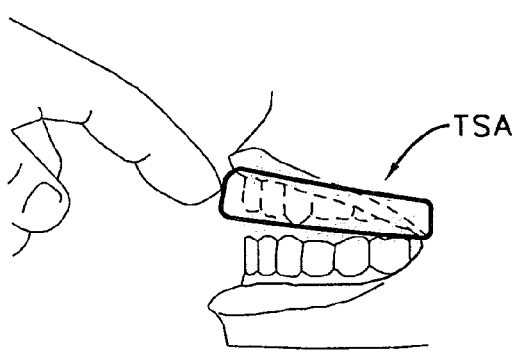
Figure 17:
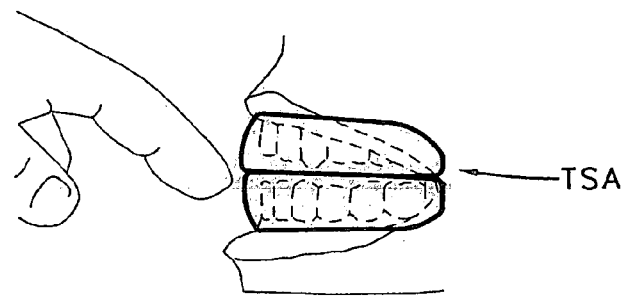

FIGS. 15, 16 and 17 show, in side elevation, tray/system/article means (TSA) for use practicing the disclosed invention method placed into a subject's (SUB) mouth so as to contact bottom, top and both bottom and top gums respectively.

Article means for containing material for absorbing oral fluids with oral composition which absorbs oral fluids therewithin can then be characterized by being at least one selection from the group consisting of:

a single sided tray/system/article means for contacting one dental arch, or portion thereof;

a double sided tray/system/article means for contacting two dental arches, or portions thereof;

a single or double sided tray/system/article means for contacting one dental arch, or portions thereof, in which is present an absorbent insertable matrix;

a single or double sided tray/system/article means for contacting one dental arch, or portions thereof, in which is present an absorbent insertable matrix comprised of a sealed sequence of moistening and solids materials which can be mixed by, for instance, a subject biting down thereupon;

a single or double sided tray/system/article means for contacting one dental arch, or portions thereof, which comprises a handle;

a single or double sided tray/system/article means for contacting one dental arch, or portions thereof, which comprises a breathing tube;

a single or double sided tray/system/article means for contacting one dental arch, or portions thereof, which comprises multiplicity of pockets therein for use in securing oral composition;

a single or double sided tray/system/article means for contacting one dental arch, or portions thereof, which comprises multiplicity of pockets therein which are shaped and positioned to accept a subject's teeth;

a single or double sided tray/system/article means for contacting one dental arch, or portions thereof, which comprises a multiplicity of projections extending therefrom;

a single or double sided tray/system/article means for contacting one dental arch, or portions thereof, which comprises a multiplicity of bristles projecting therefrom.

a single or double sided tray/system/article means for contacting one dental arch, or portions thereof, which is comprised of a material into which is impregnated oral composition;

a single or double sided tray/system/article means for contacting one dental arch, or portions thereof, which comprises a liner therewithin similar to those applied in teeth whitening;

a single or double sided tray/system/article means for contacting one dental arch, or portions thereof, which comprises liner piece of material which is folded to form a "V" shape;

a single or double sided tray/system/article means for contacting one dental arch, or portions thereof, which comprises suction means for removing oral fluids incorporated thereinto;

a single or double sided tray/system/article means for contacting one dental arch, or portions thereof, which comprises a linear "H" shaped article which is flexible and can be shaped to fit a subject's upper and/or lower dental arch;

a partial single or double sided tray/system/article means for contacting one dental arch, or portions thereof for treating one or more specific portions of a subject's upper and/or lower dental arches.

It is noted that the terminology "oral composition" can be taken to mean any composition for topical application in the oral cavity of a subject which serves to clean and/or care for oral tissue as well as the teeth. Representative of oral compositions are hygiene related products such as those delivering therapeutic and cosmetic benefits in oral cavities, including those comprising mouth wash and rinses, pastes, gels, powders, gums, strips and the like, which can be formed from at least one selection from the group:

sodium bicarbonate;
potassium bicarbonate;
sodium containing compound(s) other than sodium bicarbonate;
potassium containing compound(s) other than potassium bicarbonate;
mixture of potassium bicarbonate and psyllium husk fiber;
a mixture of sodium bicarbonate and psyllium husk fiber;
calcium containing material;
ascorbic acid;
psyllium husk fiber;
starch;
cellulose;
lignin;
hemicelluloses (pentosans);
insoluable pectins;
enzyme resistant starches;
soluble gums;
soluble pectins;
soluble polysaccharides;
rice bran;
soy fiber;

beet fiber;
pea fiber;
apple pectin;
starch;
cellulose;
xanthan gums;
gum arabic;
wheat glutin;
rye glutin;
barley glutin;
oat glutin;
typically in combination with a wetting, (ie. moistening), agent such as a selection from the group:
sorbitol;
xylitol;
potable water;
hydrogen peroxide;
alcohol
glycerine;
a subject's oral fluid which serves as a moistening agent.

Many possible benefits from use of oral compositions in the disclosed invention method are identified elsewhere in this Specification, but it is noted here that they can include supression or elimination of dental calculi, and prevention or treatment of dental disorders such as caries, periodontitis and gingivitis and elimination of halitosis.

It is further disclosed that following application of above identified, or other, materials which contain hydroxide, a follow-on step of delivering calcium containing material to the teeth of a subject can be practiced. The presence of a material comprising hydroxide in the presence of an increased amount of crevicular fluid causes OH⁻ ions to contact the teeth. This has been found to dislodge plaque build-up on the teeth, thereby providing a relatively clean tooth surface. Placing calcium containing material in contact with said relatively clean tooth surface can promote recalicification of the teeth.

As mentioned, the terminology "system" or "article" or "tray" means are all utilized substantially interchangably in this Specification.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of promoting oral hygiene, teeth whitening and recalcification in a subject in need thereof, comprising the steps of:
   a) identifying a subject having at least one upper and/or lower dental arch to be treated, said dental arch comprising gums, teeth and a crevice at which said gums and teeth meet;
   b) providing an oral fluid absorbing material and means for containing said material, wherein said material comprises a calcium-containing material and psyllium husk fiber, said material optionally further comprising sodium bicarbonate and/or potassium-bicarbonate, said means being sized and shaped to fit said dental arch;
   c) positioning said means to directly contact said dental arch with said oral fluid absorbing material; and
   d) maintaining said material in contact with said at least one dental arch, wherein said contact induces increased crevicular flow.

2. A method of promoting oral hygiene, teeth whitening and recalcification in a subject in need thereof, comprising the steps of:
   a) identifying a subject having at least one upper and/or lower dental arch to be treated, said dental arch comprising gums, teeth and a crevice at which said gums and teeth meet;
   b) providing an oral fluid absorbing material and means for containing said material, wherein said material comprises psyllium husk fiber and optionally further comprising a bicarbonate selected from the group consisting of sodium bicarbonate and potassium bicarbonate, said means being sized and shaped to fit said dental arch;
   c) positioning said means to directly contact said dental arch with said oral fluid absorbing material;
   d) maintaining said material in contact with said at least one dental arch, wherein said contact induces increased crevicular flow; and
   e) subsequently applying a calcium-containing material to said teeth.

\* \* \* \* \*